(12) United States Patent
Edwards et al.

(10) Patent No.: US 10,070,882 B2
(45) Date of Patent: Sep. 11, 2018

(54) APPARATUS AND METHOD FOR CUTTING TISSUE

(71) Applicant: Gyrus ACMI, Inc., Southborough, MA (US)

(72) Inventors: Kevin C. Edwards, Olive Branch, MS (US); Jay A. Casey, Memphis, TN (US)

(73) Assignee: Gyrus ACMI, Inc., Southborough, MA (US)

( * ) Notice: Subject to any disclaimer, the term of this patent is extended or adjusted under 35 U.S.C. 154(b) by 870 days.

(21) Appl. No.: 14/463,757

(22) Filed: Aug. 20, 2014

(65) Prior Publication Data
US 2016/0051276 A1 Feb. 25, 2016

(51) Int. Cl.
*A61B 17/32* (2006.01)
*A61B 17/00* (2006.01)

(52) U.S. Cl.
CPC ......... *A61B 17/32002* (2013.01); *A61B 2017/00309* (2013.01); *A61B 2017/00336* (2013.01); *A61B 2017/320024* (2013.01); *A61B 2017/320032* (2013.01); *A61B 2217/005* (2013.01); *A61B 2217/007* (2013.01)

(58) Field of Classification Search
CPC .... A61B 17/32002; A61B 2017/00309; A61B 2017/320032; A61B 2017/00336; A61B 2217/007; A61M 2025/0073
USPC ........................................................ 606/180
See application file for complete search history.

(56) References Cited

U.S. PATENT DOCUMENTS

| | | | |
|---|---|---|---|
| 2,464,988 A | | 3/1949 | Payne |
| 2,512,749 A | * | 6/1950 | McCloskey .............. F16J 15/36 277/383 |
| 3,802,322 A | | 4/1974 | Johnson et al. |
| 4,378,119 A | | 3/1983 | Luxford et al. |
| 4,568,313 A | | 2/1986 | Diffenderfer et al. |
| 4,634,434 A | * | 1/1987 | Marino, Jr. ....... A61M 5/16881 138/46 |
| 4,844,486 A | | 7/1989 | Schiemann |
| 4,998,527 A | | 3/1991 | Meyer |
| 5,133,387 A | | 7/1992 | Pietrykowski et al. |
| 5,152,744 A | | 10/1992 | Krause et al. |
| 5,286,253 A | | 2/1994 | Fucci |
| 5,403,334 A | | 4/1995 | Evans et al. |
| 5,593,416 A | | 1/1997 | Donahue |
| 5,601,586 A | | 2/1997 | Fucci et al. |

(Continued)

FOREIGN PATENT DOCUMENTS

| | | |
|---|---|---|
| EP | 0926992 | 3/2012 |
| JP | 08177875 | 7/1996 |

(Continued)

*Primary Examiner* — Christopher L Templeton
*Assistant Examiner* — Majid Jamialahmadi
(74) *Attorney, Agent, or Firm* — Pandiscio & Pandiscio

(57) ABSTRACT

A cutting instrument comprising:
an outer tube comprising a distal end and a proximal end;
an inner tube rotatably disposed within said outer tube, said inner tube comprising a distal end, a proximal end and a region intermediate said distal end and said proximal end, said region comprising a plurality of slits formed in said inner tube so as to render said region of said inner tube flexible; and
a bellows disposed adjacent to said plurality of slits so as to render said region of said inner tube fluid-tight.

13 Claims, 10 Drawing Sheets

(56) References Cited

U.S. PATENT DOCUMENTS

| | | |
|---|---|---|
| 5,651,781 A | 7/1997 | Grace |
| 5,899,915 A | 5/1999 | Saadat |
| 8,523,239 B2 | 9/2013 | Jung |
| 2002/0062873 A1 | 5/2002 | Nakagawa et al. |
| 2008/0114206 A1 | 5/2008 | Edwards |
| 2008/0300579 A1* | 12/2008 | Broehl ............. A61B 17/07207 606/1 |
| 2011/0022069 A1* | 1/2011 | Mitusina .......... A61B 17/32002 606/180 |
| 2012/0109130 A1 | 5/2012 | Casey et al. |
| 2012/0253324 A1 | 10/2012 | Lee et al. |
| 2013/0041392 A1 | 2/2013 | Edwards |
| 2013/0053830 A1 | 2/2013 | Edwards et al. |
| 2013/0226274 A1 | 8/2013 | Weitzig et al. |

FOREIGN PATENT DOCUMENTS

| | | |
|---|---|---|
| JP | 11013887 | 1/1999 |
| WO | WO 96/025103 | 8/1996 |
| WO | WO 98/017187 | 4/1998 |
| WO | WO 01/022889 | 4/2001 |
| WO | WO 08/031245 | 3/2008 |
| WO | WO 12/060959 | 5/2012 |

* cited by examiner

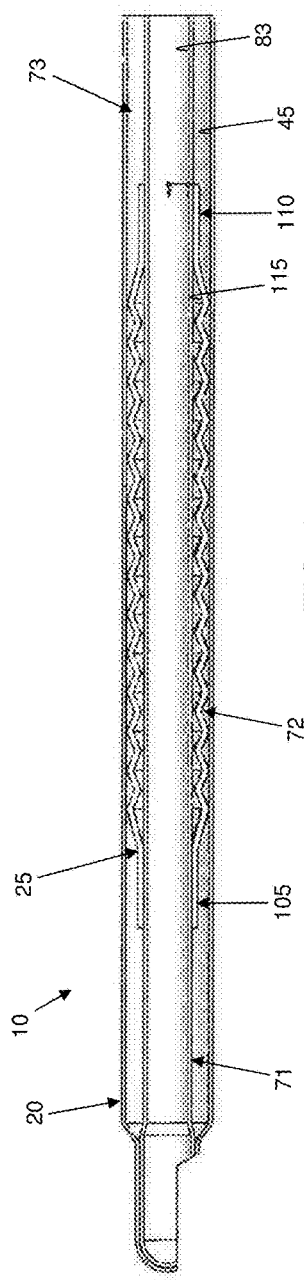
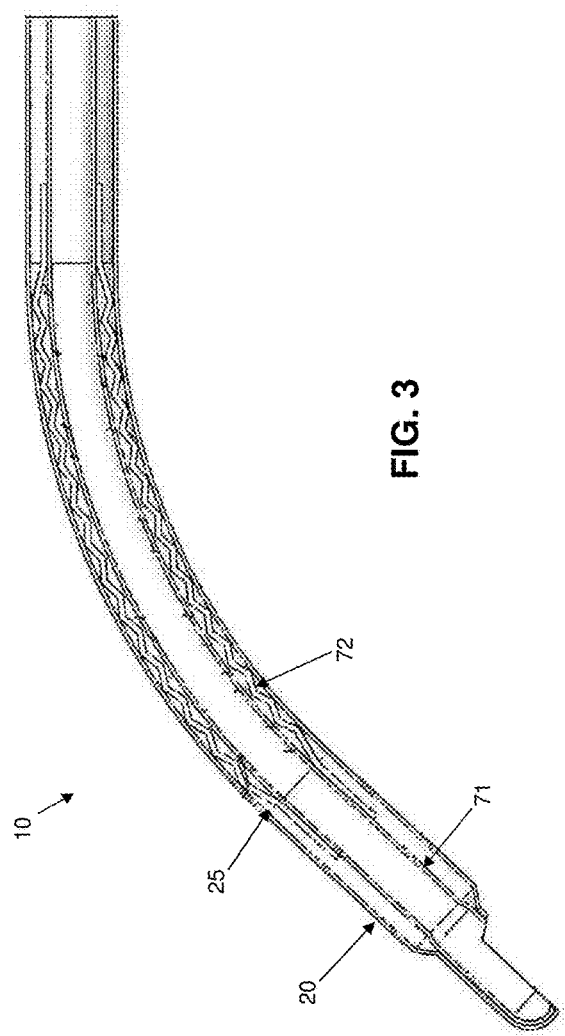
FIG. 2
FIG. 3

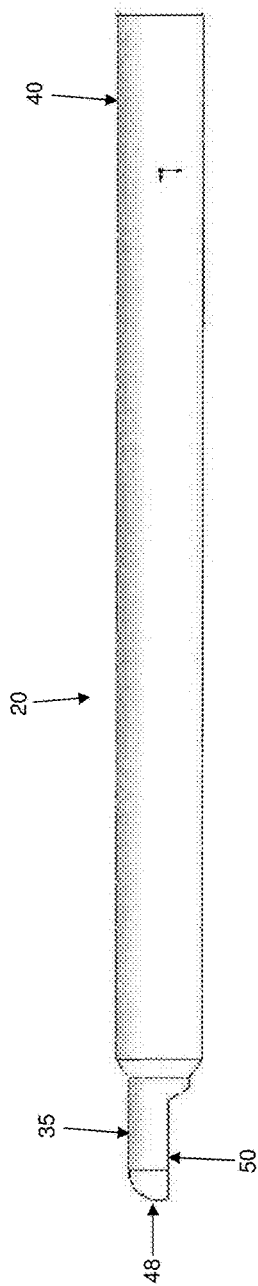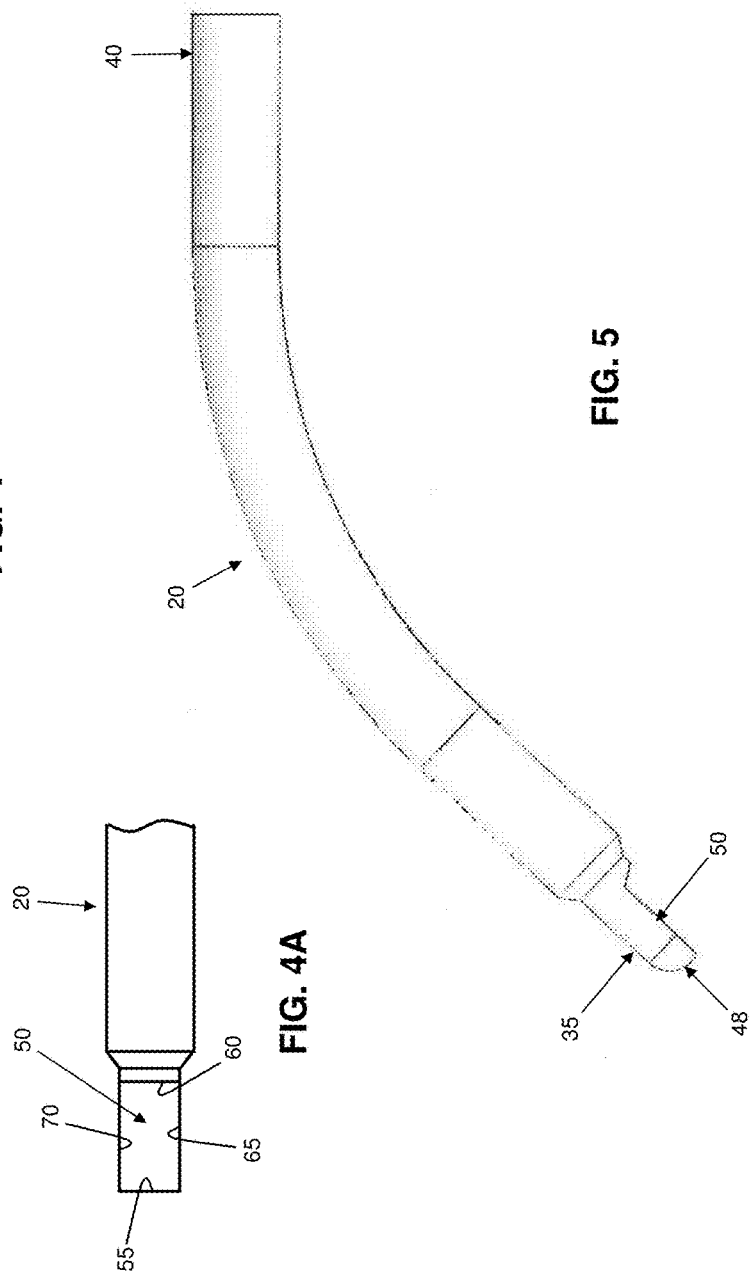

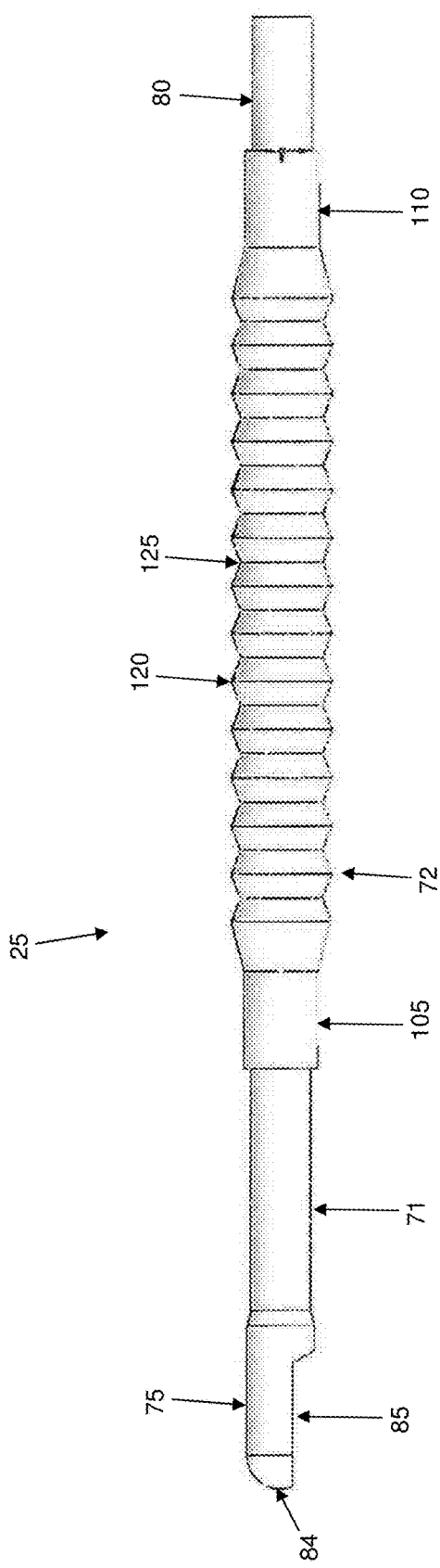
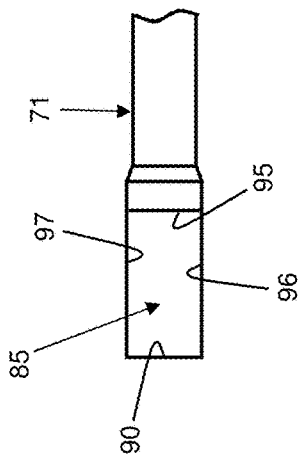
FIG. 6
FIG. 6A

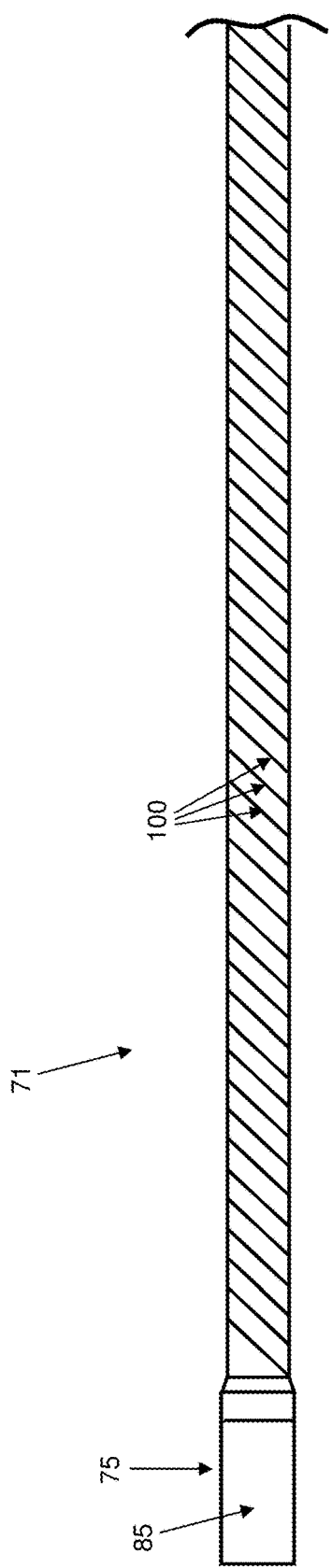

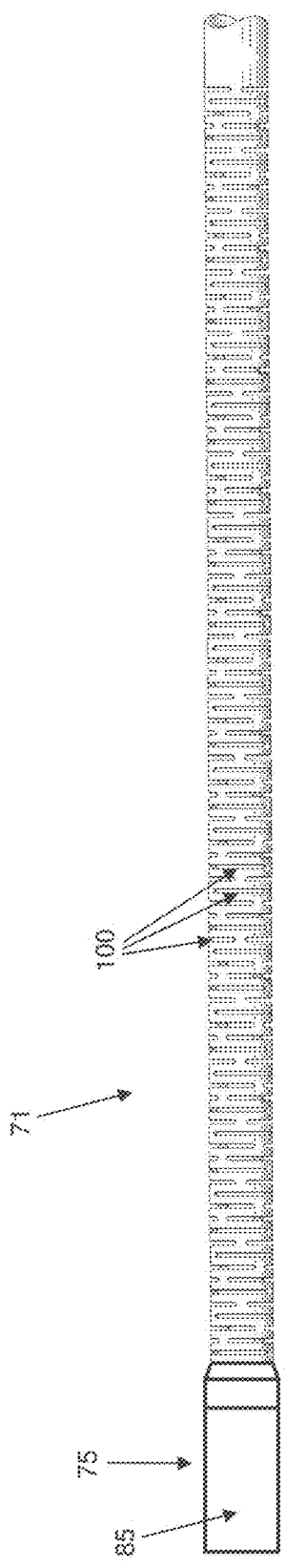
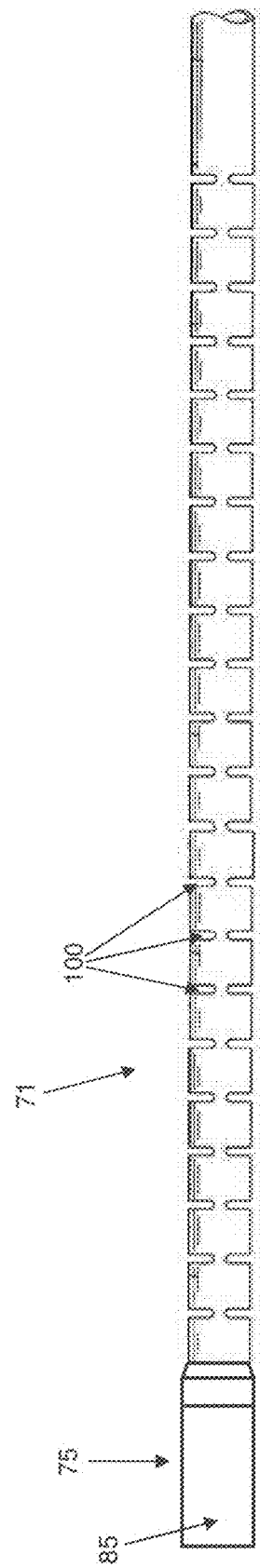
FIG. 8A
FIG. 8B

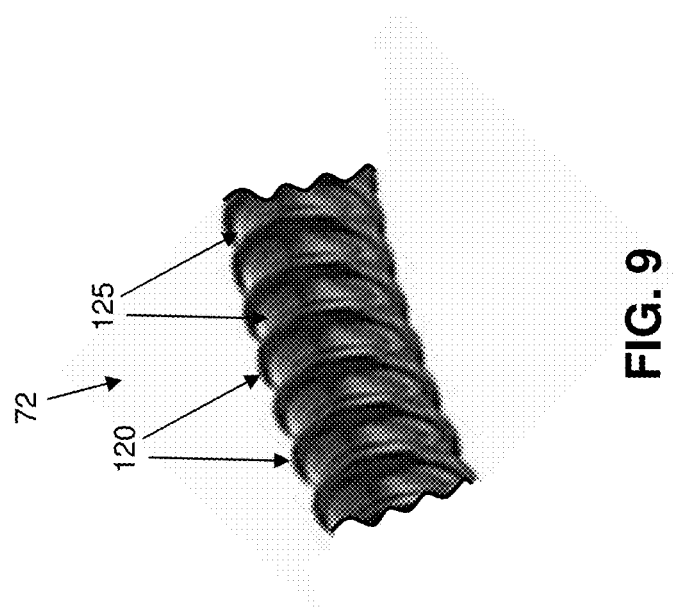

APPARATUS AND METHOD FOR CUTTING TISSUE

FIELD OF THE INVENTION

This invention relates to surgical apparatus and methods in general, and more particularly to surgical apparatus and methods for cutting tissue.

BACKGROUND OF THE INVENTION

In many situations, tissue may need to be accessed at a remote surgical site, excised from the adjacent anatomy and then the excised tissue removed from the remote surgical site. By way of example but not limitation, during arthroscopic surgery, endoscopic surgery, ENT surgery, etc., relatively small visualization devices (e.g., "scopes") and relatively small surgical tools (e.g., graspers, cutters, cauterizers, etc.) may be introduced into a restricted portion of the human body (e.g., the interior of a joint, the interior of the abdomen, the interior of a nasal passage, etc.) and then used at that location for a specific surgical procedure (e.g., to trim meniscal cartilage in a joint, to excise a tissue mass in the abdomen, to excise a tissue mass in a nasal passage, etc.).

In many such surgeries, fluid may be introduced into the surgical site (and thereafter removed from the surgical site) so as to distend the anatomy for better access and/or visualization (e.g., so as to distend the knee joint for better access and/or visualization), and/or to improve visibility (e.g., so as to flush away blood), and/or to remove debris (e.g., so as to remove severed tissue by suction.)

One of the surgical tools frequently employed in such surgeries is the so-called "powered shaver". Powered shavers typically comprise an outer tube having a window, and an inner tube rotatably disposed within the outer tube and having an opening, wherein rotation of the inner tube within the outer tube causes the opening of the inner tube to repetitively sweep across the window of the outer tube, whereby to shear off tissue extending into the window of the outer tube and the opening of the inner tube. Suction is typically applied to the interior of the inner tube so as to remove the tissue sheared off by the powered shaver.

Ideally, in addition to providing the aforementioned cutting action, the powered shaver is also able to provide either irrigation or suction to the remote surgical site, as desired by the surgeon, or to simultaneously provide both irrigation and suction to the remote surgical site.

In one construction, irrigation fluid is supplied to the gap between the interior of the outer tube and the exterior of the inner tube so that the irrigation fluid can be used to distend the anatomy and/or flush away blood and/or debris, and the irrigation fluid (and/or blood and/or debris) is removed from the surgical site by suction which is applied to the interior of the inner tube. In this way, the powered shaver is able to provide irrigation, cutting and suction in a single device.

Unfortunately, in many situations it may be desirable to form the powered shaver with a curved (i.e., non-linear) configuration. In this situation, the inner tube must be flexible in order to allow the inner tube to rotate about a curved axis (i.e., the curved axis of the outer tube), but must also be able to transmit torque along its length so as to enable cutting.

One approach for forming a flexible, torque-transmitting inner tube for the powered shaver is to form the inner tube with a plurality of slits extending through the side wall of the inner tube—these slits enable the inner tube to flex as it rotates about a curved axis while still allowing torque to be transmitted along the length of the inner tube.

Unfortunately, providing slits in the inner tube of a powered shaver is problematic where irrigation fluid is to be supplied to the surgical site through the gap between the interior of the outer tube and the exterior of the inner tube, and where suction is to be applied to the surgical site through the interior of the inner tube, since the slits in the inner tube effectively create a "short circuit" between the irrigation and suction lines, thereby undermining the irrigation and suction functions. Therefore, it can be problematic to provide a powered shaver which can provide irrigation, cutting and suction in a single device, and which has a curved (i.e., non-linear configuration).

Also, in situations where suction is to be applied to the surgical site through the interior of the inner tube without supplying irrigation fluid to the surgical site through the gap between the interior of the outer tube and the exterior of the inner tube, the provision of slits in the inner tube may compromise suction effectiveness at the surgical site (i.e., the suction force at the distal end of the inner tube is reduced since the slits in the inner tube allow the suction source to pull through the wall of the inner tube from the gap between the interior of the outer tube and the exterior of the inner tube).

A similar problem occurs where irrigation fluid is to be applied to the surgical site through the interior of the inner tube without applying suction to the gap between the interior of the outer tube and the exterior of the inner tube.

Thus it would be advantageous to provide a new powered shaver which is able to provide, either independently or simultaneously, irrigation, cutting and/or suction in a single device, and which may have a curved (i.e., non-linear) configuration. Furthermore, it would be advantageous to provide a new powered shaver which may have a curved (i.e., non-linear) configuration, wherein the new powered shaver comprises an outer tube and an inner tube rotatably disposed within the outer tube, with the lumen of the inner tube being fluidically sealed from the gap between the exterior of the inner tube and the interior of the outer tube.

SUMMARY OF THE INVENTION

The present invention comprises the provision and use of a novel powered shaver which is able to provide, either independently or simultaneously, irrigation, cutting and/or suction in a single device, and which may have a curved (i.e., non-linear) configuration.

The present invention also comprises the provision and use of a new powered shaver which may have a curved (i.e., non-linear) configuration, wherein the new powered shaver comprises an outer tube and an inner tube rotatably disposed within the outer tube, with the lumen of the inner tube being fluidically sealed from the gap between the exterior of the inner tube and the interior of the outer tube.

In one form of the invention, there is provided a cutting instrument comprising:

an outer tube comprising a distal end and a proximal end;

an inner tube rotatably disposed within said outer tube, said inner tube comprising a distal end, a proximal end and a region intermediate said distal end and said proximal end, said region comprising a plurality of slits formed in said inner tube so as to render said region of said inner tube flexible; and a bellows disposed adjacent to said plurality of slits so as to render said region of said inner tube fluid-tight.

In another form of the invention, there is provided a method for cutting an object, said method comprising:
providing a cutting instrument comprising:
an outer tube comprising a distal end and a proximal end;
an inner tube rotatably disposed within said outer tube, said inner tube comprising a distal end, a proximal end and a region intermediate said distal end and said proximal end, said region comprising a plurality of slits formed in said inner tube so as to render said region of said inner tube flexible; and
a bellows disposed adjacent to said plurality of slits so as to render said region of said inner tube fluid-tight; and
rotating said inner tube relative to said outer tube in order to cut the object.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 2 and 3 are schematic views showing the blade assembly of the powered shaver shown in FIG. 1;

FIGS. 4, 4A and 5 are schematic views showing the outer tube of the blade assembly shown in FIGS. 1-3, with FIG. 4A being a schematic view showing the distal end of the outer tube of the blade assembly of FIG. 4 but with the outer tube having been rotated 90 degrees about its longitudinal axis from the position shown in FIG. 4;

FIG. 6 is a schematic view showing the inner tube subassembly of the blade assembly shown in FIGS. 1-3;

FIG. 6A is a schematic view showing the distal end of the inner tube subassembly of FIG. 6 but with the inner tube subassembly having been rotated 90 degrees about its longitudinal axis from the position shown in FIG. 6;

FIGS. 7, 7A and 8 are schematic views showing details of the inner tube subassembly shown in FIGS. 1-3 and 6;

FIGS. 8A and 8B are schematic views showing alternative inner tubes which may be used with the inner tube subassembly shown in FIGS. 1-3 and 6; and FIGS. 9 and 10 are schematic views showing an alternative form of bellows which may be utilized in the inner tube subassembly of the present invention.

DETAILED DESCRIPTION OF THE PREFERRED EMBODIMENTS

The present invention comprises the provision and use of a novel powered shaver which is able to provide, either independently or simultaneously, irrigation, cutting and/or suction in a single device, and which may have a curved (i.e., non-linear) configuration.

The present invention also comprises the provision and use of a novel powered shaver having a curved (i.e., non-linear) configuration, wherein the new powered shaver comprises an outer tube and an inner tube rotatably disposed within the outer tube, with the lumen of the inner tube being fluidically sealed from the gap between the exterior of the inner tube and the interior of the outer tube.

Figure 1:
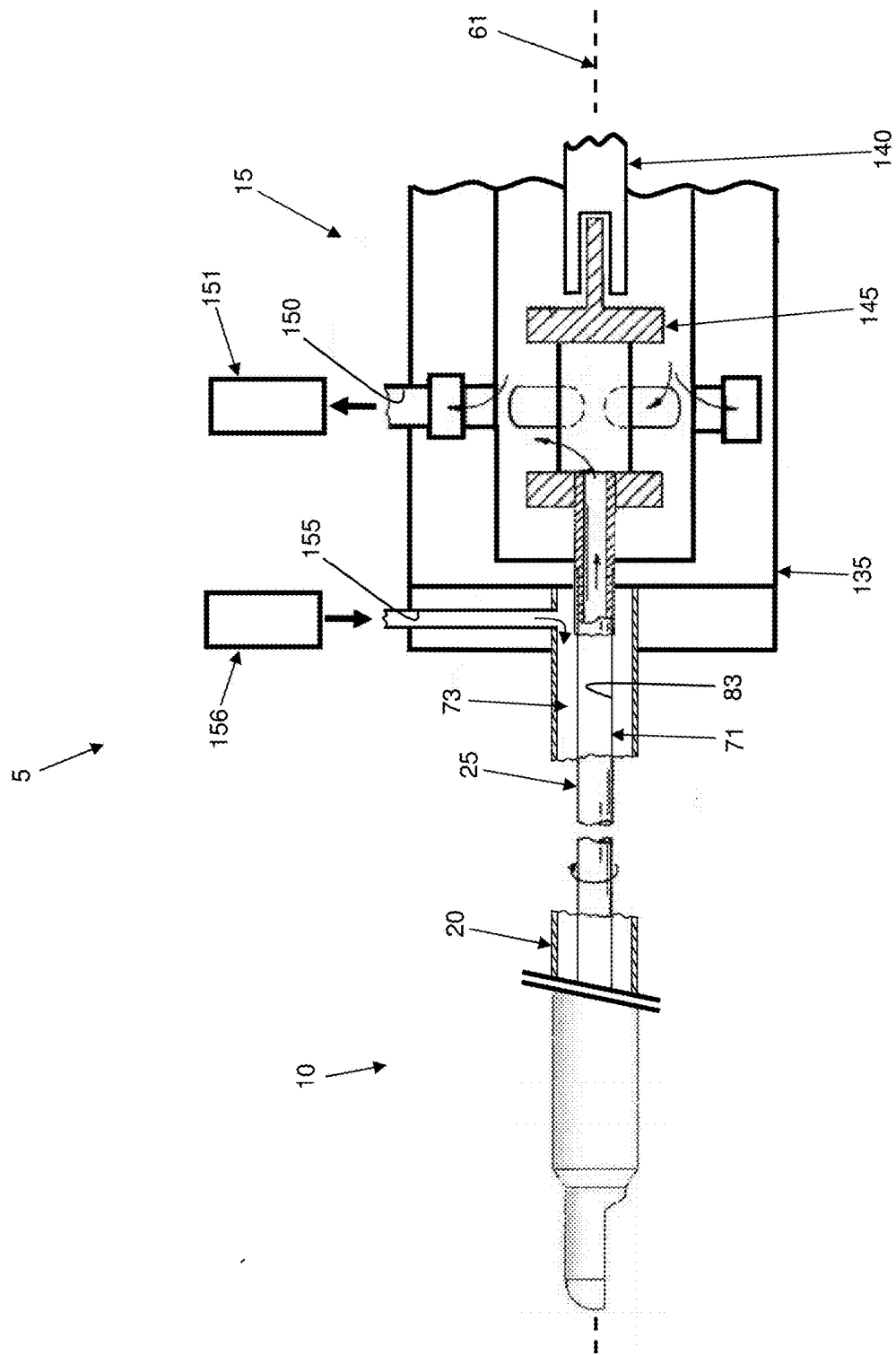
FIG. 1 is a schematic view showing a novel powered shaver formed in accordance with the present invention.

More particularly, and looking now at FIG. 1, there is shown a novel powered shaver 5 formed in accordance with the present invention. Novel powered shaver 5 generally comprises a blade assembly 10 and a handle assembly 15. As will hereinafter be discussed in further detail, blade assembly 10 is intended to be mated to handle assembly 15 (or another handle assembly) at the time of use, and detached from handle assembly 15 (or another handle assembly) after use (e.g., for cleaning and sterilization, repair or replacement, etc.). Alternatively, blade assembly 10 may be mated to handle assembly 15 (or another handle assembly) at the time of manufacture, e.g., such as in the case of a one-piece disposable system.

Blade assembly 10 is shown in greater detail in FIGS. 2-8. Blade assembly 10 generally comprises an outer tube 20 and an inner tube subassembly 25 rotatably disposed within outer tube 20.

Outer tube 20 is shown in greater detail in FIGS. 2-5. Outer tube 20 generally comprises a distal end 35, a proximal end 40, and a lumen 45 extending from distal end 35 to proximal end 40. In one preferred form the present invention, outer tube 20 preferably comprises a distal end surface 48.

Outer tube 20 comprises a window 50 (FIG. 4A) comprising a distal edge 55, a proximal edge 60, a first side edge 65 and a second side edge 70.

In accordance with the present invention, outer tube 20 may be curved, e.g., as shown in FIGS. 3 and 5.

Inner tube subassembly 25 is shown in greater detail in FIGS. 2, 3, 6, 7, 7A and 8. Inner tube subassembly 25 generally comprises an inner tube 71 and a bellows 72.

Inner tube 71 comprises a distal end 75, a proximal end 80, and a lumen 83 extending from distal end 75 to proximal end 80. In one preferred form of the present invention, inner tube 71 preferably comprises a distal end surface 84.

Inner tube 71 comprises an opening 85 (FIG. 6A) comprising a distal edge 90, a proximal edge 95, a first side edge 96 and a second side edge 97.

Inner tube 71 is rotatably disposed within outer tube 20 (FIGS. 2 and 3) such that rotation of inner tube 71 within outer tube 20 causes opening 85 of inner tube 71 to repetitively sweep across window 50 of outer tube 20, whereby to shear off tissue extending into window 50 of outer tube 20 and opening 85 of inner tube 71. More particularly, as inner tube 71 is rotated within outer tube 20, one or the other of first side edge 96 and second side edge 97 of inner tube 71 is swept across one or the other of first side edge 65 and second side edge 70 of outer tube 20, depending on the direction of rotation of inner tube 71 relative to outer tube 20, so as to create a shearing action at the interface of the overlapping side edges of inner tube 71 and outer tube 20. This shearing action serves to cut away tissue extending into window 50 of outer tube 20 and opening 85 of inner tube 71.

In accordance with the present invention, in order to allow inner tube 71 to be rotated within a curved outer tube 20, and also to transmit torque along its length so as to enable the aforementioned cutting action, inner tube 71 preferably also comprises a plurality of slits 100 (FIGS. 7 and 7A) which extend through the side wall of inner tube 71. Slits 100 are provided in at least the region of inner tube 71 which flexes during rotation of inner tube 71 within curved outer tube 20.

Also in accordance with the present invention, novel powered shaver 5 is able to provide, independently or simultaneously, irrigation and/or suction to the surgical site. In one preferred form of the invention, irrigation is supplied to the surgical site through the gap 73 between the interior of outer tube 20 and the exterior of inner tube 71, and suction is applied to the surgical site through the interior of inner tube 71 (i.e., through lumen 83). Alternatively, suction may be supplied to the surgical site through gap 73 (i.e., the gap between the interior of outer tube 20 and the exterior of inner tube 71), and irrigation may be applied to the surgical site through the interior of inner tube 71 (i.e., through lumen 83).

In order to prevent slits 100 in inner tube 71 from creating a "short circuit" between the irrigation and suction lines, thereby undermining the irrigation and suction functions, inner tube subassembly 25 comprises bellows 72 for effectively covering slits 100, whereby to isolate the interior of inner tube 71 from the region exterior to inner tube 71.

More particularly, and looking now at FIGS. 2, 3, 6, 7 and 8, in one form of the invention, bellows 72 comprises an elongated structure having a distal end 105, a proximal end 110 and a lumen 115 extending therebetween. Bellows 72 is mounted coaxially over inner tube 71, and its distal end 105 and proximal end 110 sealingly secured to inner tube 71, so that slits 100 in inner tube 71 are covered by bellows 72. As a result, bellows 72 sealingly isolates lumen 83 of inner tube 71 from lumen 45 of outer tube 20. At the same time, bellows 72 do not interfere with rotation of inner tube 71 within outer tube 20. Bellows 72 are sized to cover at least the portion of inner tube 71 which comprises slits 100.

Thus, where gap 73 (i.e., the gap between the interior of outer tube 20 and the exterior of inner tube 71) is used for one of irrigation and suction, and/or where the interior of inner tube 71 (i.e., lumen 83) is used for the other of irrigation and suction, bellows 72 prevent slits 100 in inner tube 71 from creating a "short circuit" between the irrigation and suction lines. At the same time, inasmuch as bellows 72 do not interfere with rotation of inner tube 71 within outer tube 20, bellows 72 do not undermine the cutting action of novel powered shaver 5.

In one preferred form of the invention, bellows 72 comprise a plurality of peaks 120 and troughs 125, wherein peaks 120 and troughs 125 extend perpendicular to the axis of bellows 72 (FIG. 6). Preferably peaks 120 are sized to contact (e.g., with a sliding fit) the interior surface of outer tube 20. Note that the contact between peaks 120 and the interior surface of outer tube 20 may be sealing, substantially sealing or non-sealing. Alternatively, if desired, peaks 120 of bellows 72 can approach but be spaced from the interior of outer tube 20.

In one preferred form of the invention, peaks 120 preferably include notches 130 (FIG. 8) for allowing fluid to easily pass between the exterior of bellows 72 and the interior of outer tube 20, as will hereinafter be discussed. Note that notches 130 may be provided regardless of whether peaks 120 contact the interior surface of outer tube 20.

As shown in FIG. 1, blade assembly 10 is intended to be mated to handle assembly 15 (or another handle assembly) at the time of use, and detached from handle assembly 15 (or another handle assembly) after use (e.g., for cleaning and sterilization, repair or replacement, etc.). Alternatively, blade assembly 10 may be mated to handle assembly 15 (or another handle assembly) at the time of manufacture, e.g., such as in the case of a one-piece disposable system.

Handle assembly 15 is provided with a housing 135 for securely mounting the distal end 40 of outer tube 20, and means for coupling a drive shaft 140 to inner tube 71, e.g., a connector 145 which is secured to inner tube 71, whereby to drivingly rotate inner tube 71 (and its associated bellows 72, not shown in FIG. 1). Preferably connector 145 is provided with appropriate ports so that the interior of inner tube 71 is in fluid communication with a port 150, whereby to deliver irrigation or suction from an irrigation or suction source 151 to blade assembly 10 via lumen 83 of inner tube 71. In one preferred form of the invention, port 150 provides suction to blade assembly 10 via lumen 83 of inner tube 71.

Handle assembly 15 is also provided with a port 155 for accessing the gap between the interior of outer tube 20 and the exterior of inner tube subassembly 25, whereby to deliver irrigation or suction from an irrigation or suction source 156 to blade assembly 10 via the gap 73 between the interior of outer tube 20 and the exterior of inner tube subassembly 25. In one preferred form of the invention, port 155 is connected to irrigation source 156 so as to provide irrigation to blade assembly 10 via the gap 73 between the interior of outer tube 20 and the exterior of inner tube subassembly 25. As noted above, in one preferred form of the invention, bellows 72 comprises notches 130 to allow fluid to pass easily between the exterior of bellows 72 and the interior of outer tube 20.

It should be appreciated that handle assembly 15 shown in FIG. 1 is provided by way of example but not limitation, and other handle assemblies may be used in conjunction with blade assembly 10.

Figure 7:
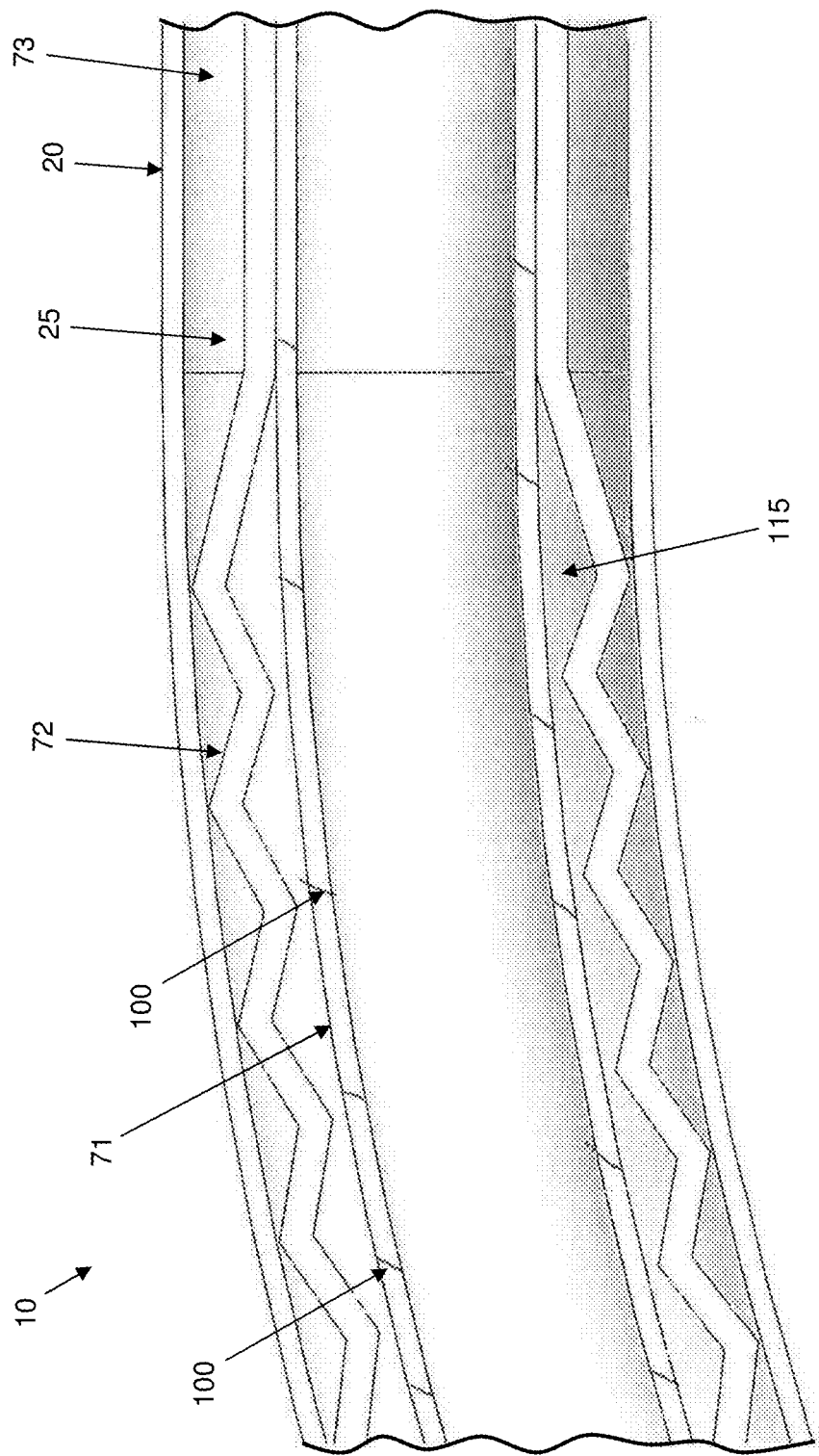
Figure 8:
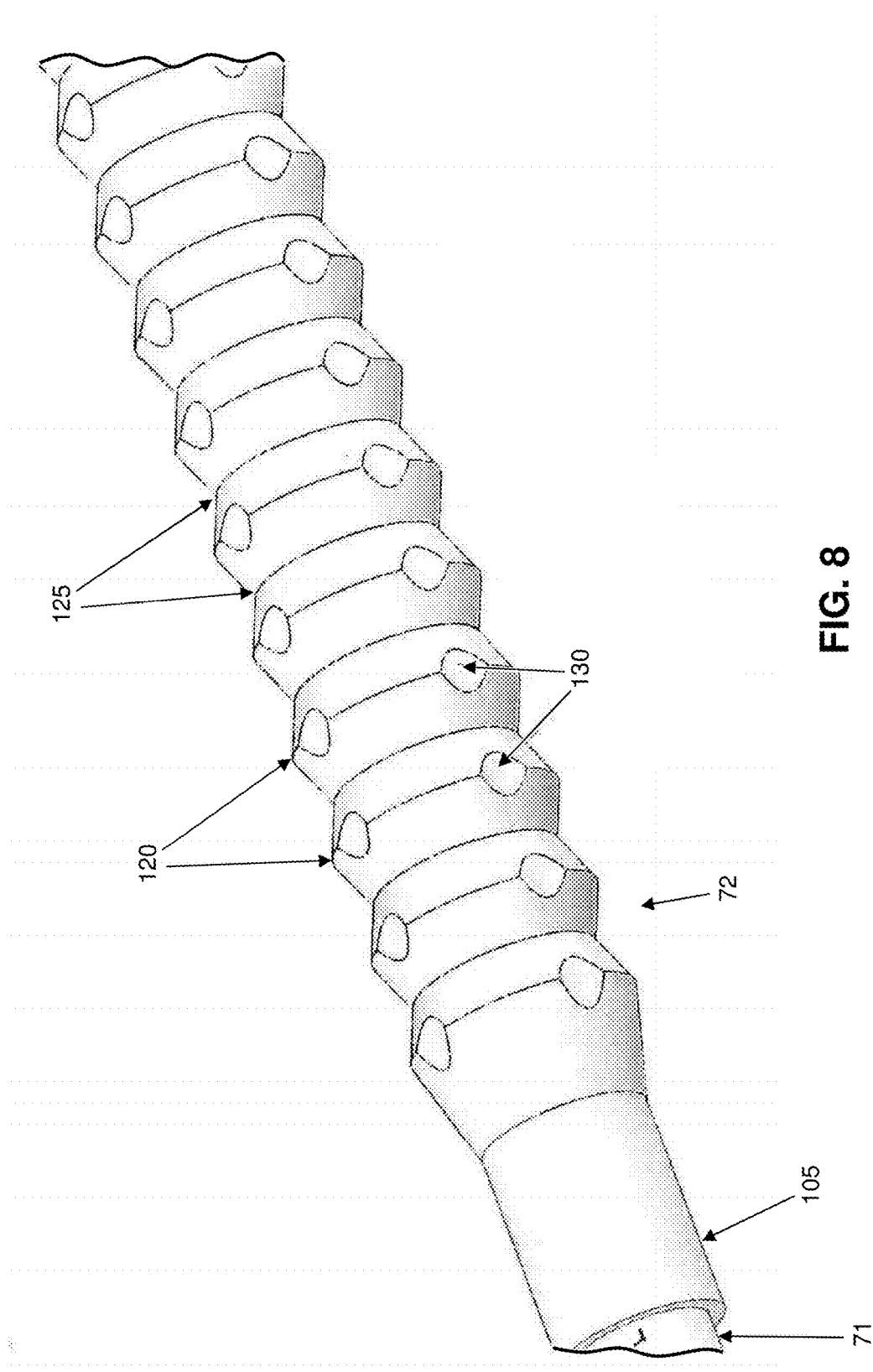

In FIGS. 7 and 7A, slits 100 of inner tube 71 are shown as following a helical path. However, if desired, other slit configurations may be utilized. By way of example but not limitation, slits 100 may extend substantially perpendicular to the longitudinal axis of inner tube 71. Thus, for example, FIG. 8A shows slits 100 extending substantially perpendicular to the longitudinal axis of inner tube 71, with the slits being circumferentially staggered from one another. FIG. 8B shows slits 100 extending substantially perpendicular to the longitudinal axis of inner tube 71, with the slits being circumferentially aligned with one another. Still other configurations will be apparent to those skilled in the art in view of the present disclosure.

Figure 10:
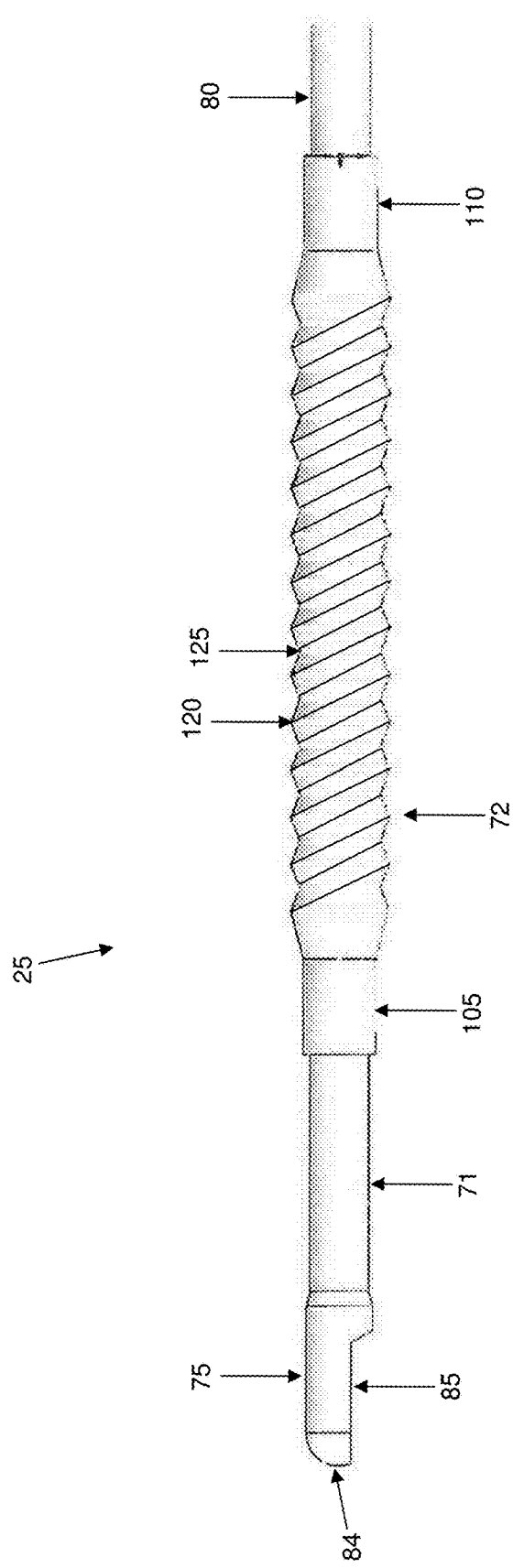

In another preferred form of the invention, and looking now at FIGS. 9 and 10, peaks 120 and troughs 125 of bellows 72 follow a helical path about the axis of bellows 72. In this form of the invention, notches 130 may be omitted, inasmuch as fluid may pass between the exterior of bellows 72 and the interior of outer tube 20 by following the helical path of troughs 125 of bellows 72.

It should be appreciated that, by forming a helical path along the length of bellows 72 between peaks 120 and troughs 125, bellows 72 may also act as a screw pump, i.e., as a mechanical transport. More particularly, rotation of inner tube 71 (and hence, rotation of bellows 72) in a first direction facilitates distal movement of material (solid or fluid) disposed in the helical path. Rotation of inner tube 71 (and hence, rotation of bellows 72) in a second, opposite direction facilitates proximal movement of material (solid or fluid) disposed in the helical path. Note that this movement of material (solid or fluid) in either direction is independent of (or in addition to) any irrigation or suction which may be provided to gap 73 by irrigation or suction source 156.

The novel powered shaver 5 of the present invention is a significant improvement in the art, since it is able to provide, either independently or simultaneously, irrigation, cutting and/or suction in a single device, where that device may have a curved (i.e., non-linear) configuration.

The novel powered shaver 5 of the present invention also provides a device having a curved (i.e., non-linear) configuration, wherein the device comprises an outer tube and an inner tube rotatably disposed within the outer tube, with the lumen of the inner tube being fluidically sealed from the gap between the exterior of the inner tube and the interior of the outer tube.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A cutting instrument comprising:
an outer tube comprising a distal end and a proximal end;
an inner tube rotatably disposed within said outer tube, said inner tube comprising a distal end, a proximal end and a region intermediate said distal end and said proximal end, said region comprising a plurality of slits formed in said inner tube so as to render said region of said inner tube flexible; and
a bellows disposed adjacent to said plurality of slits so as to render said region of said inner tube fluid-tight, said bellows comprising a distal end, a proximal end, and a longitudinal axis extending therebetween, said bellows further comprising an inner surface facing said inner tube and an outer surface facing said outer tube, said outer surface of said bellows comprising a plurality of alternating peaks and troughs, said peaks extending radially away from said longitudinal axis of said bellows so as to define a peripheral edge which lies in a plane perpendicular to the longitudinal axis of said bellows, and each of said troughs being disposed between a pair of said peaks;
wherein each of said plurality of peaks comprises at least one notch formed in the peripheral edge, whereby to fluidically connect said troughs together and thereby allow fluid to pass by said peaks.

2. A cutting instrument according to claim 1 wherein said bellows is secured to said inner tube at said distal end of said bellows and said proximal end of said bellows.

3. A cutting instrument according to claim 1 wherein said bellows is disposed exterior to said inner tube and interior to said outer tube, and further wherein the outer surface of said bellows contacts said outer tube, with said notches providing passageways between said bellows and said outer tube.

4. A cutting instrument according to claim 1 further comprising a suction source connected to said proximal end of said inner tube.

5. A cutting instrument according to claim 4 further comprising an irrigation source connected to said proximal end of said outer tube.

6. A cutting instrument according to claim 1 wherein said outer tube is curved.

7. A cutting instrument according to claim 1 wherein said outer tube is flexible.

8. A cutting instrument according to claim 1 wherein said outer tube comprises a window having a window edge, said inner tube comprises an opening having an opening edge, and said opening of said inner tube is longitudinally aligned with said window of said outer tube;
and further wherein, when said inner tube rotates relative to said outer tube, (i) during a first phase of rotation of said inner tube relative to said outer tube, said opening is rotationally aligned with said window so as to allow an object to extend into said inner tube, and (ii) during a second phase of rotation of said inner tube relative to said outer tube, said opening edge passes by said window edge so as to cut an object extending into said inner tube.

9. A method for cutting an object, said method comprising:
providing a cutting instrument comprising:
an outer tube comprising a distal end and a proximal end;
an inner tube rotatably disposed within said outer tube, said inner tube comprising a distal end, a proximal end and a region intermediate said distal end and said proximal end, said region comprising a plurality of slits formed in said inner tube so as to render said region of said inner tube flexible; and
a bellows disposed adjacent to said plurality of slits so as to render said region of said inner tube fluid-tight, said bellows comprising a distal end, a proximal end, and a longitudinal axis extending therebetween, said bellows further comprising an inner surface facing said inner tube and an outer surface facing said outer tube, said outer surface of said bellows comprising a plurality of alternating peaks and troughs, said peaks extending radially away from said longitudinal axis of said bellows so as to define a peripheral edge which lies in a plane perpendicular to the longitudinal axis of said bellows, and each of said troughs being disposed between a pair of said peaks;
wherein each of said plurality of peaks comprises at least one notch formed in the peripheral edge, whereby to fluidically connect said troughs together and thereby allow fluid to pass by said peaks; and
rotating said inner tube relative to said outer tube in order to cut the object.

10. A method according to claim 9 further comprising a suction source connected to said proximal end of said inner tube.

11. A method according to claim 10 further comprising an irrigation source connected to said proximal end of said outer tube.

12. A method according to claim 9 wherein at least one of said outer tube and said inner tube comprises a cutting surface.

13. A method according to claim 9 wherein said outer tube comprises a window having a window edge, said inner tube comprises an opening having an opening edge, and said opening of said inner tube is longitudinally aligned with said window of said outer tube;
and further wherein, when said inner tube rotates relative to said outer tube, (i) during a first phase of rotation of said inner tube relative to said outer tube, said opening is rotationally aligned with said window so as to allow an object to extend into said inner tube, and (ii) during a second phase of rotation of said inner tube relative to said outer tube, said opening edge passes by said window edge so as to cut an object extending into said inner tube.

* * * * *